US00PP22713P2

(12) United States Plant Patent
Olesen

(10) Patent No.: US PP22,713 P2
(45) Date of Patent: May 8, 2012

(54) GROUND COVER ROSE PLANT NAMED 'POULCOT010'

(50) Latin Name: *Rosa hybrid*
Varietal Denomination: Poulcot010

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 12/930,441

(22) Filed: Jan. 7, 2011

(51) Int. Cl.
*A01H 5/00* (2006.01)

(52) U.S. Cl. ..... Plt./102

(58) Field of Classification Search ..... Plt./102
See application file for complete search history.

*Primary Examiner* — Annette Para

(57) ABSTRACT

A new garden rose plant of the ground cover class which has abundant, yellow-orange flowers and attractive foliage. This new and distinct variety has shown to be uniform and stable in the resulting generations from asexual propagation.

3 Drawing Sheets

Botanical designation: *Rosa* hybrid.
Variety denomination: 'Poulcot010'.

SUMMARY OF THE INVENTION

The present invention constitutes a new and distinct variety of garden rose plant which originated from a controlled crossing between the female seed parent, an unnamed, non-commercial seedling, and the male pollen parent, also an unnamed, non-commercial seedling.

The two parents were crossed during the summer of 1999 and the resulting seeds were planted in a controlled environment in Fredensborg, Denmark. The new variety, named 'Poulcot010', originated as a single seedling from the stated cross.

The new variety may be distinguished from its female seed parent primarily by flower color. The seed parent has yellow flowers, while 'Poulcot010' has a blend of yellow and orange.

The new variety may be distinguished from its male pollen parent by flower form and color. The pollen parent has yellow flowers while 'Poulcot010' has yellow-orange blend flowers. The pollen parent's flower has more petals than 'Poulcot010'.

The objective of the hybridization of this rose variety was to create a new and distinct variety for garden use with unique qualities, such as:

1. Uniform and abundant yellow-orange single petal flowers;
2. Vigorous, but compact growth when propagated both as a budded rose and on its own roots;
3. Exceptional disease resistance; and
4. Abundant rose hips.

This combination of qualities is not present in previously available commercial cultivars of this type, known to the inventor, and distinguish 'Poulcot010' from all other varieties of which we are aware.

As part of the rose development program, Mogens N. Olesen germinated the seeds from the aforementioned hybridization during winter of 1999 and conducted evaluations on the resulting seedlings in a controlled environment in Fredensborg, Denmark. 'Poulcot010' was selected in the spring of 2000 by the inventor as a single plant from the progeny of the aforementioned hybridization.

Asexual reproduction of 'Poulcot010' by traditional budding and rooted cuttings was first done by Mogens N. Olesen in the nursery in Fredensborg, Denmark in July, 2000. This initial and other subsequent asexual propagations conducted in controlled environments have demonstrated that the characteristics of 'Poulcot010' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, and stems, of the new variety. Specifically illustrated in the drawings are.

DETAILED DESCRIPTION OF THE VARIETY

Figure 1:
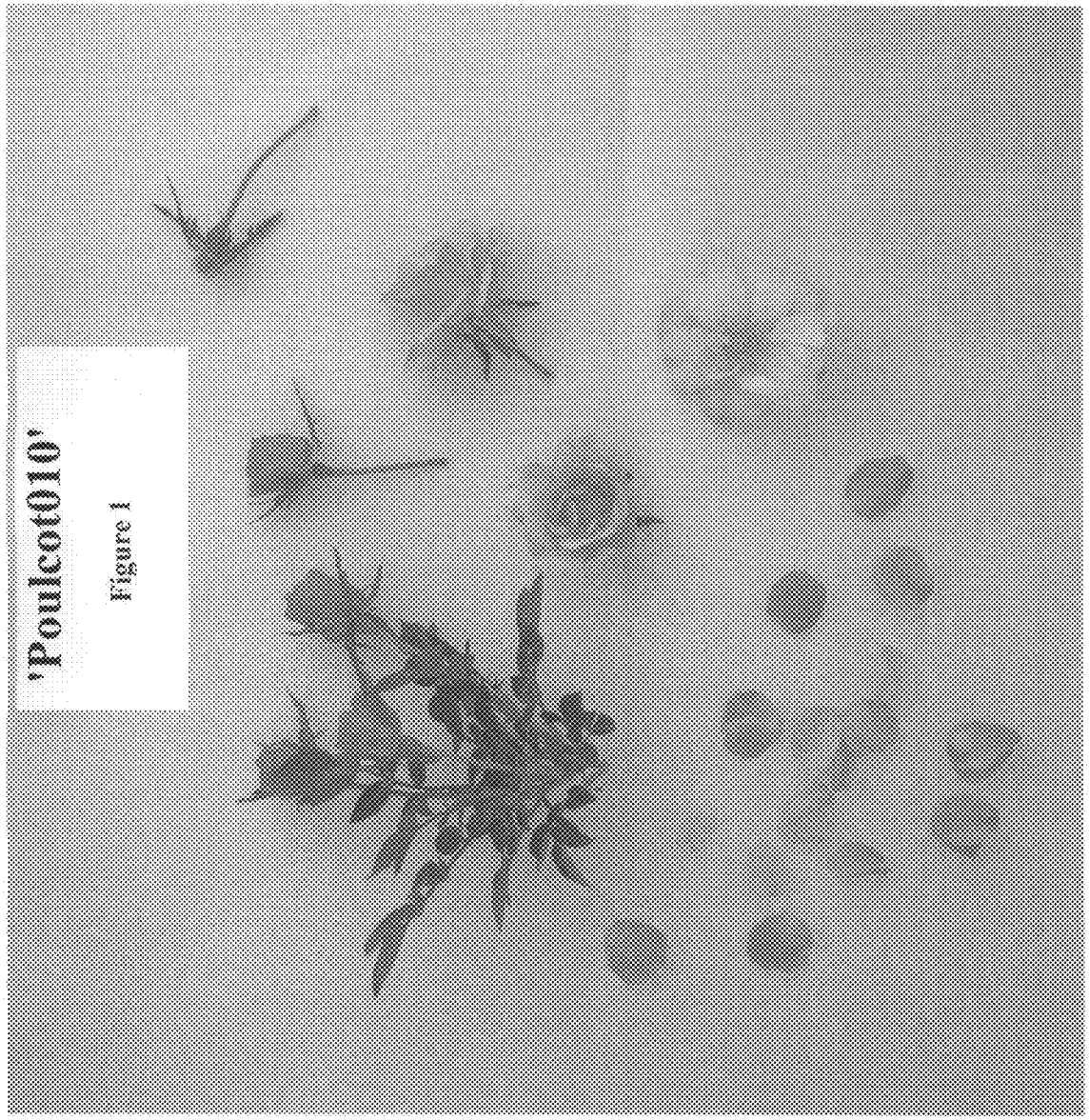
FIG. 1: Open flowers, petals detached.
Figure 2:
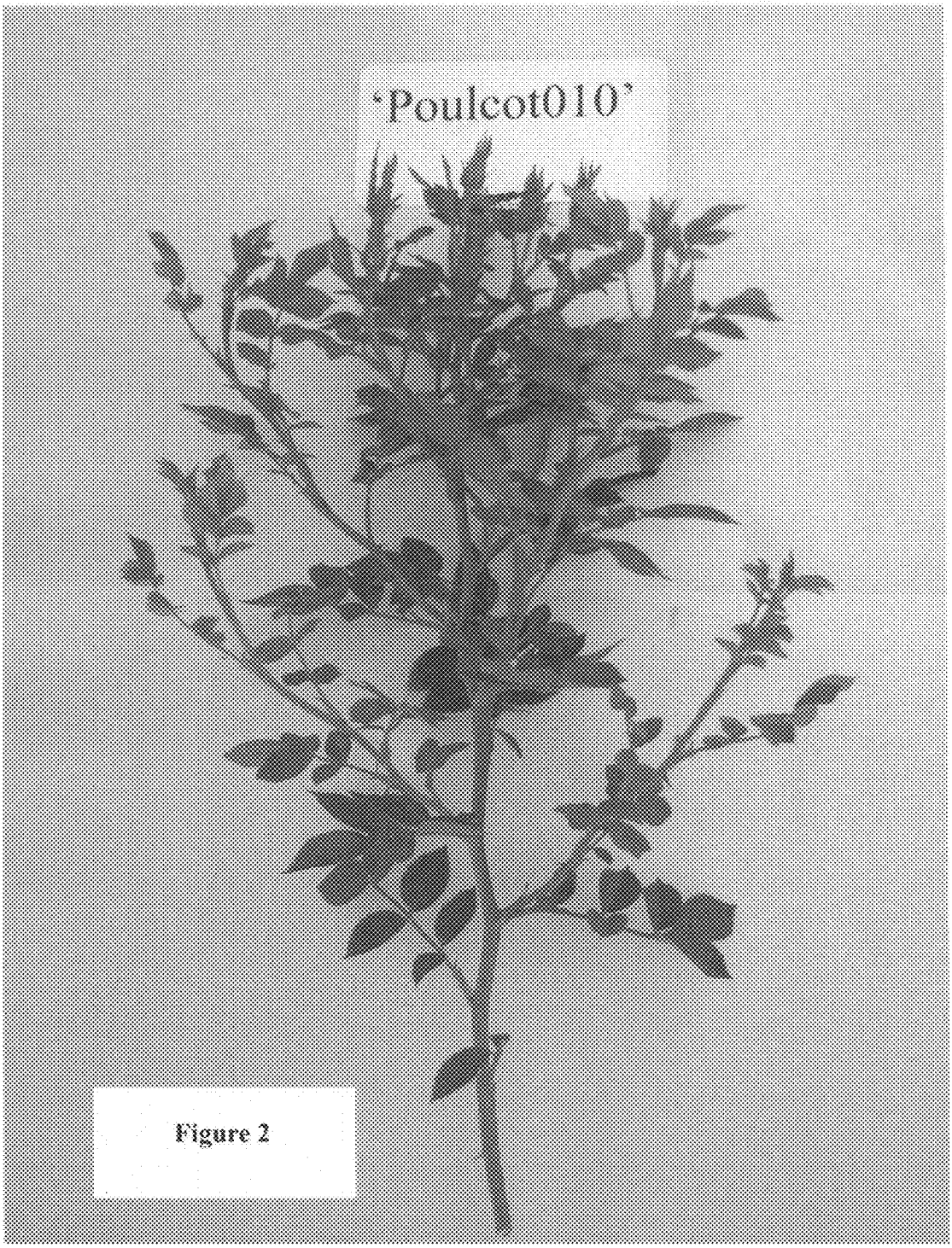
FIG. 2: Flowering branch, showing arrangement of flower buds and stem.
Figure 3:
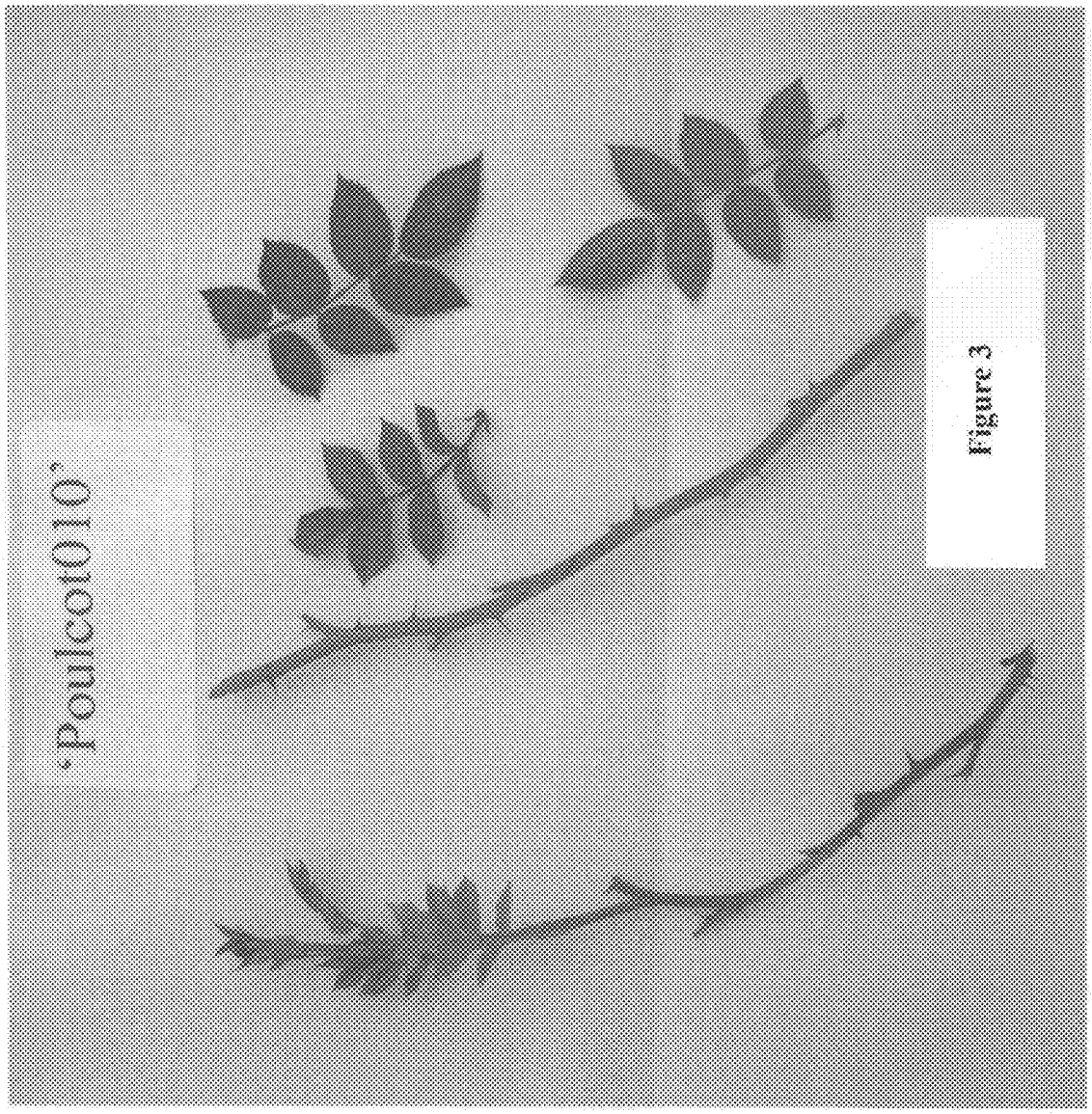
FIG. 3: Bare stems and leaves.

The following is a description of 'Poulcot010', as observed in its growth in in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulcot001', U.S. Plant Pat. No. 16,303 are compared to 'Poulcot010' in Chart 1.

CHART 1

| | 'Poulcot010' | 'Poulcot001' |
|---|---|---|
| Petal Count | 15 petals | 20 to 25 petals |
| General Tonality of Flower Color | On open flower Yellow Group 13C with intonations of Orange-Red Group 35A | On open flower Yellow Group 5C. |

FLOWER AND FLOWER BUD

Blooming habit: Continuous.

Flower bud:

*Size*.—Upon opening, 15 mm in length from base of receptacle to end of bud. Bud diameter is typically 8 mm.

*Bud form*.—Urceolate.

*Bud color*.—As sepals unfold, petals are Red Group 46C.

*Sepal inner surface*.—Color: Green Group 138C and Yellow-Green Group 14A. Moderate anthocyanic intonations of Greyed-Purple Group 183A observed. Surface: Smooth, weakly pubescent.

*Sepal outer surface*.—Color: Yellow-Green Group 146A. Anthocyanic pigments the color of Greyed-Purple Group 183A observed. Texture: Rough with stipitate glands.

*Sepal shape*.—Apex: Cirrhose. Base: Flat at union with receptacle.

*Sepal margin*.—Margins have strong foliaceous appendages on three of the five sepals.

*Sepal size*.—25 mm long by 10 mm wide on average.

*Receptacle*.—Texture: Smooth. Shape: Elliptical. Size: 5 mm tall by 4 mm wide. Color: Yellow-Green Group 146B.

*Peduncle*.—Length: 30 to 30 cm. Diameter: 3 mm on average. Color: Yellow-Green Group 144B with moderate anthocyanic intonations the color of Greyed-Red Group 181A.

*Pedicel*.—Surface: Rough with small prickles. Length: 30 mm on average. Diameter: 2 mm on average. Color: Yellow-Green Group 144C. Anthocyanic pigments the color of Greyed-Red Group 180B observed. Strength: Weak.

Flower bud development: Flowers are borne on panicles, consisting of 5 to 7 flower buds per flowering branch.

Flower bloom:

*Fragrance*.—Moderate spicy rose scent.

*Duration*.—The blooms have a duration on the plant of approximately 5 to 7 days. Petals fall cleanly away from plant after flowers have fully matured.

*Size*.—Flower diameter is 40 to 50 mm when open. Flower depth is 10 to 15 mm.

*Flower shape*.—General shape is single, becoming almost flat when fully opened.

*Shape of flower, side view*.—Open flowers are shaped like a flattened convex on the upper portion, concave on the lower portion.

Petalage: Under normal conditions, flowers have 15 petals total, approximately 3 of which are petaloids.

Petal color:

*Upon opening, petals*.—Upper surface: Yellow-Orange Group 14A with marginal intonations of Red Group 42B. No distinctive coloration at the petal base observed. Lower surface: Red Group 43B. Occasional streaks running along the mid vein of petals, the color of Yellow-Orange Group 18A.

*After opening, petals*.—Upper surface: Yellow-Orange Group 14C with intonations of Orange Group 25C and Red Group 42D at margins. No distinctive coloration at the petal base observed. Lower surface: Orange-Red Group 32C with intonations of Red Group 45D. Streaks of Yellow-Orange Group 11A occasionally.

General tonality: On open flower Yellow Group 13C with intonations of Orange-Red Group 35A.

Petals:

*Petal reflex*.—Flat.

*Margin*.—Entire with small point at the center. Moderate undulations of margin observed.

*Shape*.—Generally broad elliptic. Apex shape: Cuspidate. Base shape: Rounded.

*Size*.—Outer petals are 20 mm (l)×20 mm (w). Inner petals are 20 mm (l)×15 mm (w).

*Texture*.—Smooth.

*Thickness*.—Average.

Petaloids:

*Quantity*.—3 on average.

*Shape*.—Irregular, acute apex and base.

*Color*.—Upper surface is Yellow-Orange Group 14A with marginal intonations of Red Group 42B. No distinctive coloration at the petaloid base observed. Lower surface is Red Group 43B. Occasional streaks running along the mid vein of petaloids, the color of Yellow-Orange Group 18A.

*Size*.—15 mm (l)×10 mm (w).

Reproductive organs:

*Pollen*.—None observed.

*Anthers*.—Size: 2 mm in length. Color: Yellow-Orange Group 13B. Quantity: 35 on average.

*Filaments*.—Color: Yellow-Orange Group 13B. Length: 5 mm.

*Pistils*.—Length: 3 mm. Quantity: 25 on average.

*Stigmas*.—Inferior in location relative to the length of the filaments and the height of the anthers. Color: Yellow Group 4D.

*Styles*.—Color: Yellow Group 4D.

*Hips*.—None Observed in the field nursery in Jackson County Oreg.

PLANT

Plant growth: Arching and spreading. When grown as a budded field grown plant on *Rosa multiflora* understock, the average height of the plant is 100 cm and the average width is 110 cm.

Stems:

*Color*.—Juvenile growth: Yellow-Green Group 144B with anthocyanic intonations the color of Greyed-Purple Group 183B. Mature growth: Yellow-Green Group 144B.

*Length*.—On average, canes are 60 cm from the base of the plant to the flowering portion.

*Diameter*.—6 mm.

*Internodes*.—On mature canes, there is an average distance of 30 mm between nodes.

*Surface texture*.—Young wood: Smooth. Older wood: Smooth.

Prickles:

*Incidence*.—9 prickles per 10 cm of stem.

*Size*.—Average length of prickles on mature stems is 11 mm.

*Shape*.—Convex at the lower portion, linear above.

*Color*.—Juvenile prickles: Greyed-Purple Group 185B. Mature prickles: Greyed-Yellow Group 160C.

Plant foliage: Normal number of leaflets leaves in middle of the stem: 7 leaflets.

*Compound leaf*.—90 mm (l)×45 (w) on average.

*Quantity*.—3 leaves per 10 cm of stem on average.

*Leaf bearing angle to the stem*.—45 degrees.

*Color of mature foliage*.—Upper side: Yellow-Green Group 147A. Lower side: Yellow-Green Group 146B.

*Color of juvenile foliage*.—Upper side: Yellow-Green Group 144A. Lower side: Yellow-Green Group 144A. Anthocyanin: Margins, the color of Greyed-Purple Group 183B.

Plant leaves and leaflets:

*Stipules*.—Size: 15 mm in length on average. Quantity: 2 per compound leaf. Shape: Linear, slightly broad based with outward extending apecies. Margins: Finely serrated with many stipitate glands. Color: Yellow-Green Group 146A.

*Petiole*.—Length: 22 mm on average. Diameter: 2 mm.

*Upper surface*.—Color: Yellow-Green Group 147A. Observations: Numerous stipitate glands.

*Lower surface*.—Color: Yellow-Green Group 147B. Observations: Numerous small prickles observed.

*Rachis*.—Length: 45 mm on average. Upper surface: Color: Yellow-Green Group 147A with anthocyanic intonations the color of Greyed-Purple Group 183A. Observations: Numerous stipitate glands.

*Lower surface*.—Color: Yellow-Green Group 147B. Observations: Numerous small prickles observed.

*Leaflet*.—Edge: Serrated. Size: Average size of the terminal leaflet on normal leaves is 35 mm in length by 15 mm wide. Shape: Generally lanceolate. Base: Acute. Apex: Acuminate. Texture: Smooth. Thickness: Thick. Arrangement: Odd pinnate. Venation: Reticulate. Glossiness: Very Glossy.

Disease resistance: Above average resistance to powdery and downy mildew, rust, black spot, and Botrytis under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the ground cover rose class named 'Poulcot010', substantially as illustrated and described herein, due to its abundant yellow-orange blend flowers, disease resistance, and extended period of bloom.

* * * * *